(12) United States Patent
Hansmann et al.

(10) Patent No.: US 7,201,737 B2
(45) Date of Patent: Apr. 10, 2007

(54) TREATMENT OF VASCULAR OCCLUSIONS USING ELEVATED TEMPERATURES

(75) Inventors: Douglas R. Hansmann, Bainbridge Island, WA (US); Peter R. Rule, Los Altos, CA (US)

(73) Assignee: Ekos Corporation, Bothell, WA (US)

( * ) Notice: Subject to any disclaimer, the term of this patent is extended or adjusted under 35 U.S.C. 154(b) by 0 days.

(21) Appl. No.: 11/046,209

(22) Filed: Jan. 28, 2005

(65) Prior Publication Data

US 2005/0240151 A1    Oct. 27, 2005

Related U.S. Application Data

(60) Provisional application No. 60/564,382, filed on Apr. 22, 2004, provisional application No. 60/540,035, filed on Jan. 29, 2004.

(51) Int. Cl.
*A61F 7/12* (2006.01)
(52) U.S. Cl. ..................................................... 604/113
(58) Field of Classification Search ............ 604/19–20, 604/500, 915, 96.01, 113–114; 606/27, 194; 607/96, 98–99, 100–105
See application file for complete search history.

(56) References Cited

U.S. PATENT DOCUMENTS

| | | | |
|---|---|---|---|
| 4,754,752 A * | 7/1988 | Ginsburg et al. ............. 606/27 |
| 4,921,478 A * | 5/1990 | Solano et al. ................ 604/509 |
| 5,129,883 A * | 7/1992 | Black .................... 604/101.03 |
| 5,158,071 A | 10/1992 | Umemura et al. |
| 5,197,946 A | 3/1993 | Tachibana |
| 5,269,291 A | 12/1993 | Carter |
| 5,318,014 A | 6/1994 | Carter |
| 5,362,309 A | 11/1994 | Carter |
| 5,368,036 A | 11/1994 | Tanaka et al. |
| 5,380,273 A | 1/1995 | Dubrul et al. |
| 5,405,322 A * | 4/1995 | Lennox et al. ................ 606/28 |
| 5,474,531 A | 12/1995 | Carter |
| 5,558,092 A | 9/1996 | Unger et al. |
| 5,620,479 A | 4/1997 | Diederich |
| 5,628,728 A | 5/1997 | Tachibana et al. |
| 5,630,837 A | 5/1997 | Crowley |
| 5,713,848 A | 2/1998 | Dubrul et al. |
| 5,728,062 A | 3/1998 | Brisken |
| 5,735,811 A | 4/1998 | Brisken |

(Continued)

FOREIGN PATENT DOCUMENTS

EP    1252885    10/2002

(Continued)

*Primary Examiner*—Manuel Mendez
(74) *Attorney, Agent, or Firm*—Knobbe, Martens, Olson & Bear LLP

(57) ABSTRACT

A method for providing a therapeutic effect to a treatment site within a patient's vasculature comprises positioning a catheter at the treatment site. The catheter includes a heating element and a fluid delivery lumen that is coupled to an exit port within a distal region of the catheter. The method further comprises passing the therapeutic compound through the delivery lumen and the exit port at a flow rate. The heated therapeutic compound is provided to the treatment site. The method further comprises exposing at least a portion of the treatment site and at least a portion of the delivered heated therapeutic compound to ultrasonic energy generated by the ultrasound radiating member.

20 Claims, 12 Drawing Sheets

U.S. PATENT DOCUMENTS

| | | | |
|---|---|---|---|
| 5,836,896 A | 11/1998 | Rosenschein | |
| 5,916,192 A | 6/1999 | Nita et al. | |
| 5,935,124 A | 8/1999 | Klumb et al. | |
| 5,997,497 A | 12/1999 | Nita et al. | |
| 6,001,069 A | 12/1999 | Tachibana et al. | |
| 6,024,718 A | 2/2000 | Chen et al. | |
| 6,033,397 A * | 3/2000 | Laufer et al. | 606/27 |
| 6,053,868 A | 4/2000 | Geistert et al. | |
| 6,078,830 A | 6/2000 | Levin et al. | |
| 6,096,000 A | 8/2000 | Tachibana et al. | |
| 6,113,558 A | 9/2000 | Rosenschein et al. | |
| 6,176,842 B1 | 1/2001 | Tachibana et al. | |
| 6,190,315 B1 | 2/2001 | Kost et al. | |
| 6,190,355 B1 * | 2/2001 | Hastings | 604/96.01 |
| 6,206,831 B1 | 3/2001 | Suorsa et al. | |
| 6,210,356 B1 | 4/2001 | Anderson et al. | |
| 6,228,046 B1 | 5/2001 | Brisken | |
| 6,231,516 B1 | 5/2001 | Keilman et al. | |
| 6,287,271 B1 | 9/2001 | Dubrul et al. | |
| 6,296,619 B1 | 10/2001 | Brisken et al. | |
| 6,299,597 B1 * | 10/2001 | Buscemi et al. | 604/101.03 |
| 6,387,052 B1 | 5/2002 | Quinn et al. | |
| 6,511,478 B1 | 1/2003 | Burnside et al. | |
| 6,542,767 B1 | 4/2003 | McNichols et al. | |
| 6,635,017 B1 | 10/2003 | Moehring et al. | |
| 6,723,063 B1 | 4/2004 | Zhang et al. | |
| 6,758,857 B2 | 7/2004 | Cioanta et al. | |
| 2001/0025190 A1 | 9/2001 | Weber et al. | |
| 2003/0220568 A1 | 11/2003 | Hansmann et al. | |
| 2004/0019318 A1 | 1/2004 | Wilson et al. | |
| 2004/0024347 A1 | 2/2004 | Wilson et al. | |
| 2004/0049148 A1 | 3/2004 | Rodriguez et al. | |

FOREIGN PATENT DOCUMENTS

| | | |
|---|---|---|
| JP | H02-180275 | 7/1990 |
| WO | WO 99/34858 | 7/1999 |

* cited by examiner

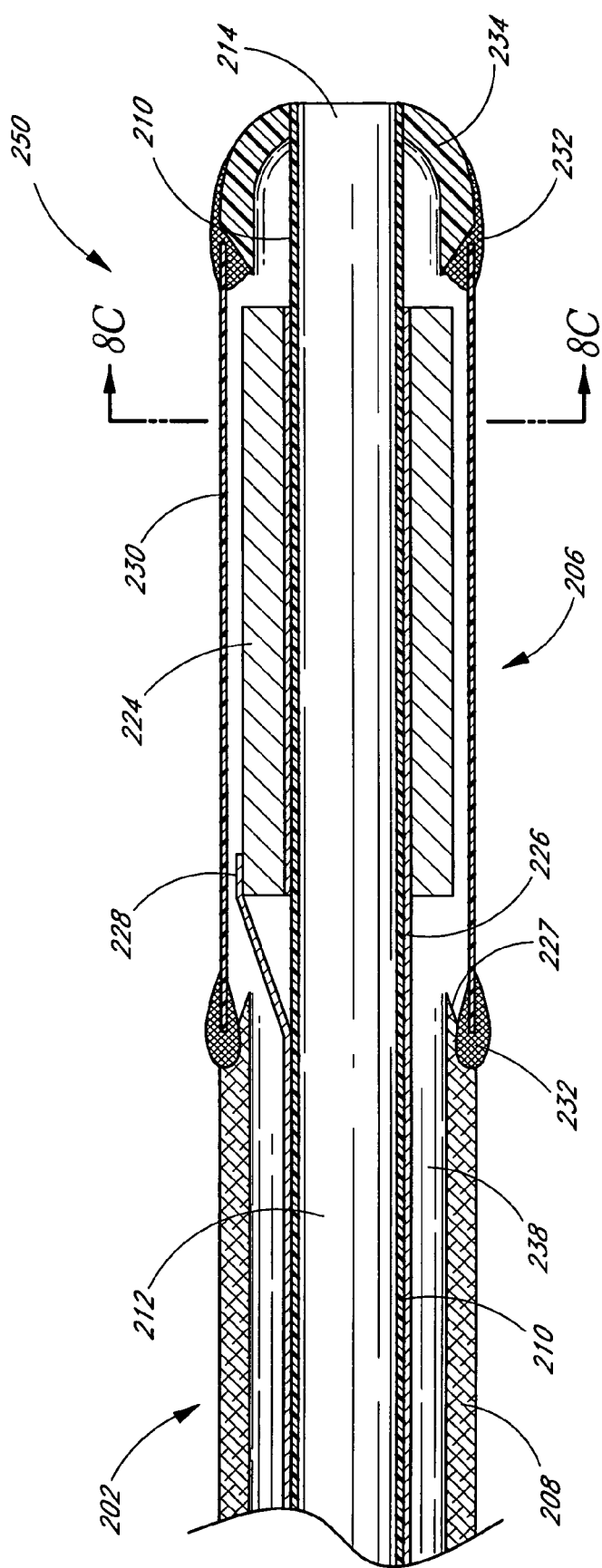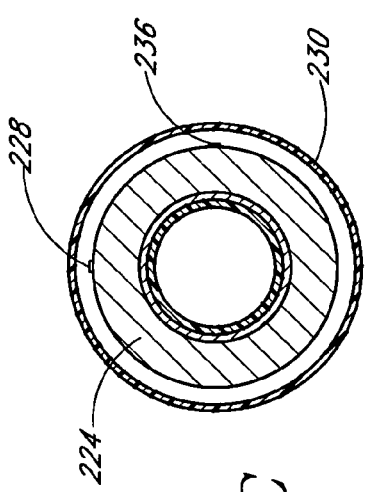
FIG. 8B
FIG. 8C

TREATMENT OF VASCULAR OCCLUSIONS USING ELEVATED TEMPERATURES

This application claims the benefit of U.S. Provisional Patent Application 60/540,035 (filed 29 Jan. 2004); and U.S. Provisional Patent Application 60/564,382 (filed 22 Apr. 2004).

FIELD OF THE INVENTION

The present invention relates generally to treatment of vascular occlusions, and more specifically to treatment of vascular occlusions with elevated temperatures and a therapeutic compound.

BACKGROUND OF THE INVENTION

As taught in U.S. Pat. No. 6,001,069, catheters can be used to treat human blood vessels that have become partially or completely occluded by plaque, thrombi, emboli or other substances that reduce the blood carrying capacity of the vessel. To remove or reduce the occlusion, the catheter is used to deliver solutions containing therapeutic compounds directly to the occlusion site. In these particular applications, ultrasonic energy generated by the ultrasound assembly is used to enhance the effect of the therapeutic compounds. Such a device can be used in the treatment of diseases such as peripheral arterial occlusion or deep vein thrombosis. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069 and 6,210,356.

The efficacy of therapeutic compounds in reducing or removing a vascular occlusion can also be enhanced by increasing the temperature of the therapeutic compound that is provided at the treatment site. For example, it has been determined that treatment of lower limb ischemia progresses more rapidly when heated rtPA is used, than when room temperature rtPA is used. See Dimitrios K. Tsetis et al., "Potential Benefits From Heating the High-Dose rtPA Boluses Used in Catheter-Directed Thrombolysis for Acute/Subacute Lower Limb Ischemia", *J Endovasc Ther* 10:739–744 (2003), the entire disclosure of which is hereby incorporated herein by reference.

SUMMARY OF THE INVENTION

According to one embodiment of the present invention, a method is provided for treating a vascular obstruction at a treatment site within a patient's vasculature system. In the method, a catheter is advanced to the treatment site. The catheter includes a treatment zone and a fluid delivery lumen that is coupled to an exit port within the treatment zone of the catheter. A therapeutic compound is passed through the fluid delivery lumen and the exit port, such that the therapeutic compound is delivered to the treatment site. The treatment site is heated to an elevated temperature.

According to another embodiment of the present invention, a catheter comprises a tubular body having a drug delivery lumen terminating at a exit port within a treatment zone. A heating element is positioned within the treatment zone. A temperature sensor is in the treatment zone. A control system is configured to maintain the treatment zone at a an elevated temperature for a specified amount of time.

BRIEF DESCRIPTION OF THE DRAWINGS

Exemplary embodiments of the vascular occlusion treatment system are illustrated in the accompanying drawings, which are for illustrative purposes only. The drawings comprise the following figures, in which like numerals indicate like parts.

FIG. 8B is a cross-sectional view of a distal end of an ultrasonic catheter configured for use within small vessels of a patient's vasculature.

FIG. 8C is a cross-sectional view of the ultrasound catheter taken through line 12B—12B of FIG. 12A.

DETAILED DESCRIPTION OF PREFERRED EMBODIMENTS

Figure 1:
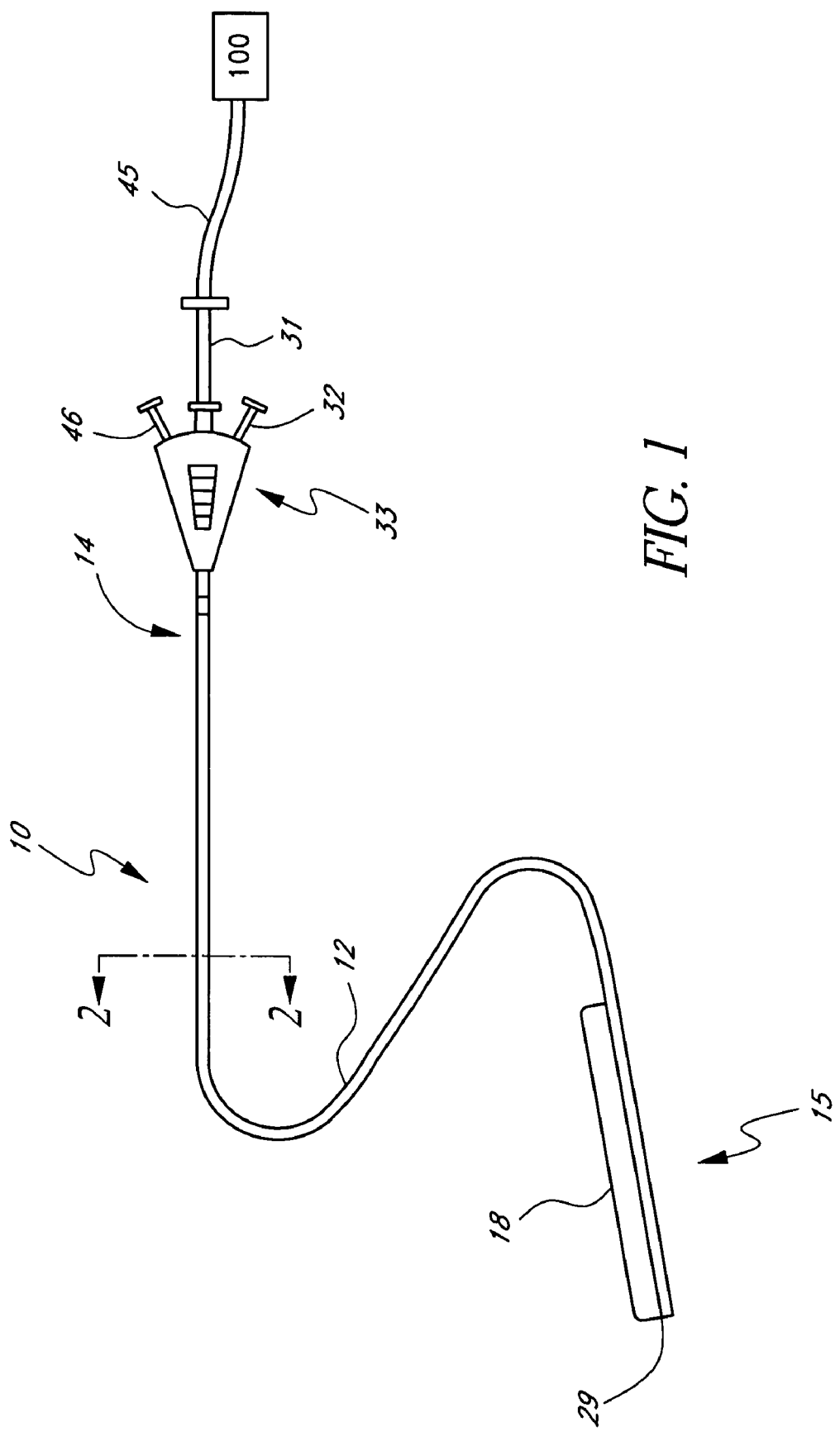
FIG. 1 is a schematic illustration of an ultrasonic catheter configured for insertion into large vessels of the human body.

As set forth above, methods and apparatuses have been developed that allow a vascular occlusion at a treatment site to be treated with a combination of a therapeutic compound and thermal energy. Disclosed herein are several exemplary embodiments of catheters that can be used to provide thermal energy and the therapeutic compound to the treatment site. Also disclosed are exemplary methods for using such catheters.

Introduction.

As used herein, the term "therapeutic compound" refers broadly, without limitation, and in addition to its ordinary meaning, to a drug, medicament, dissolution compound, genetic material or any other substance capable of effecting physiological functions. Additionally, a mixture includes substances such as these is also encompassed within this definition of "therapeutic compound". Examples of therapeutic compounds include thrombolytic compounds, anti-thrombosis compounds, and other compounds used in the treatment of vascular occlusions, including compounds intended to prevent or reduce clot formation. In applications where human blood vessels that have become partially or completely occluded by plaque, thrombi, emboli or other substances that reduce the blood carrying capacity of a vessel, exemplary therapeutic compounds include, but are not limited to, heparin, urokinase, streptokinase, tPA, rtPA and BB-10153 (manufactured by British Biotech, Oxford, UK).

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the average acoustic power of the ultrasonic energy is between about 0.01 watts and 300 watts. In one embodiment, the average acoustic power is about 15 watts.

As used herein, the term "heating element" refers broadly, without limitation, and in addition to its ordinary meaning, to any apparatus capable of elevating the temperature of the treatment site. In one embodiment, the heating element comprises an ultrasonic transducer, which converts electrical energy into ultrasonic energy and thermal energy. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. With respect to ultrasonic transducer, thermal energy is generated in two ways. First, because the ultrasonic transducer coverts electrical energy to ultrasound energy imperfectly, some portion of the electrical energy is converted to heat. In addition, it is postulated that the ultrasound filed generated by the transducer is absorbed by the surrounding biological material producing a localized elevation of temperature. In another embodiment, the heating element comprises a thermoelectric heater, such as, for example, an electrical resistive heaters. Other embodiments of an heating element include, without limitation, RF emitters, lasers, conductive heaters, convective heaters and/or the delivery of a heated fluid to the treatment site.

Overview of a Large Vessel Catheter.

FIG. 1 schematically illustrates a catheter 10 configured for use in the large vessels of a patient's anatomy. For example, the catheter 10 illustrated in FIG. 1 can be used to treat long segment peripheral arterial occlusions, such as those in the vascular system of the leg.

As illustrated in FIG. 1, the catheter 10 generally includes a multi-component, elongate flexible tubular body 12 having a proximal region 14 and a distal region 15. The tubular body 12 includes a flexible treatment zone 18 located in the distal region 15. The tubular body 12 and other components of the catheter 10 can be manufactured in accordance with a variety of techniques known to an ordinarily skilled artisan. Suitable materials and dimensions can be readily selected based on the natural and anatomical dimensions of the treatment site and on the desired percutaneous access site.

For example, in an exemplary embodiment, the tubular body proximal region 14 comprises a material that has sufficient flexibility, kink resistance, rigidity and structural support to push the treatment zone 18 through the patient's vasculature to a treatment site. Examples of such materials include, but are not limited to, extruded polytetrafluoroethylene ("PTFE"), polyethylenes ("PE"), polyamides and other similar materials. In certain embodiments, the tubular body proximal region 14 is reinforced by braiding, mesh or other constructions to provide increased kink resistance and ability to be pushed. For example, nickel titanium or stainless steel wires can be placed along or incorporated into the tubular body 12 to reduce kinking.

For example, in an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths can be used in other applications.

In an exemplary embodiment, the tubular body 12 is divided into at least three sections of varying stiffness. The first section, which includes the proximal region 14, has a relatively higher stiffness. The second section, which is located in an intermediate region between the proximal region 14 and the distal region 15, has a relatively lower stiffness. This configuration further facilitates movement and placement of the catheter 10. The third section, which includes the treatment zone 18, has a relatively lower stiffness than the second section in spite of the presence of ultrasound radiating members which can be positioned therein.

Figure 2:
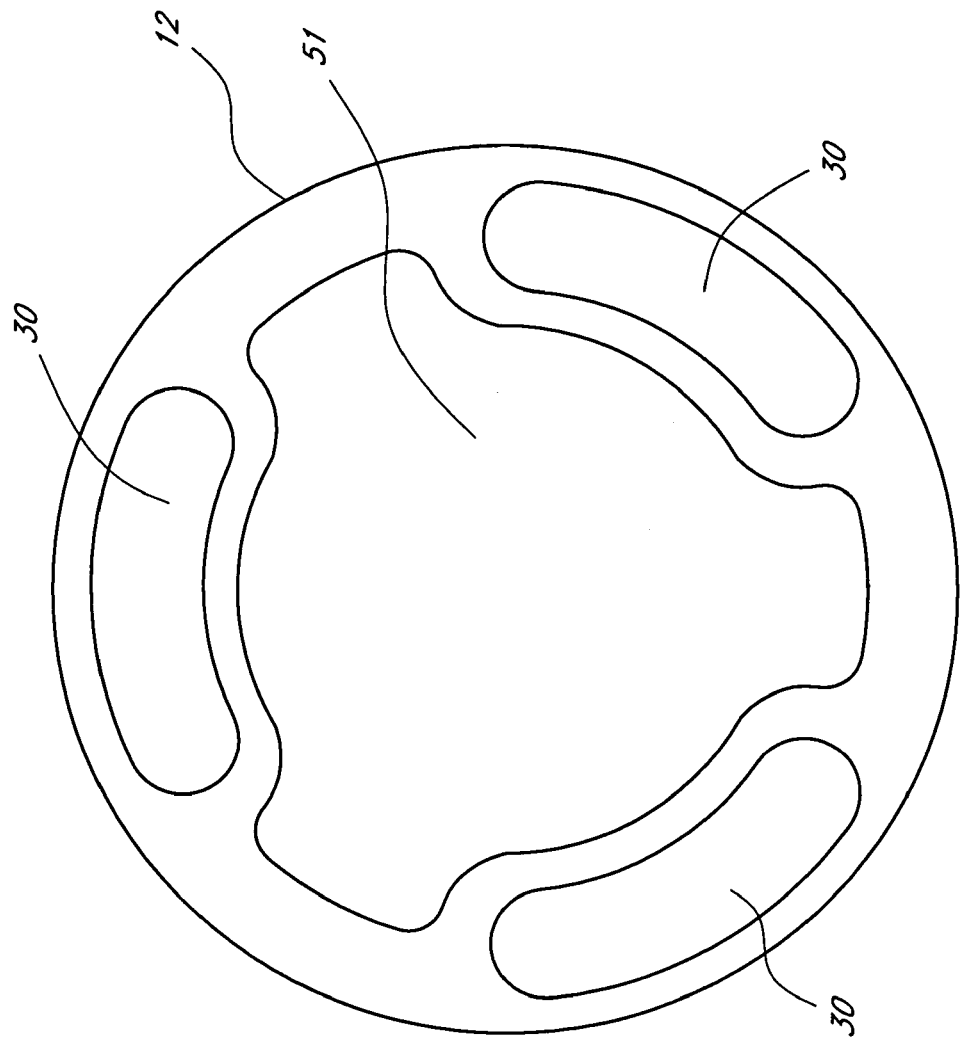
FIG. 2 is a cross-sectional view of the ultrasonic catheter of FIG. 1 taken along line 2—2.

FIG. 2 illustrates a cross section of the tubular body 12 taken along line 2—2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. In such embodiments, the arrangement of the fluid delivery lumens 30 provides a hollow central lumen 51 passing through the tubular body 12. The cross-section of the tubular body 12, as illustrated in FIG. 2, is substantially constant along the length of the catheter 10. Thus, in such embodiments, substantially the same cross-section is present in both the proximal region 14 and the distal region 15 of the tubular body 12, including the energy delivery section 18.

In certain embodiments, the central lumen 51 has a minimum diameter greater than about 0.030 inches. In another embodiment, the central lumen 51 has a minimum diameter greater than about 0.037 inches. In an exemplary embodiment, the fluid delivery lumens 30 have dimensions of about 0.026 inches wide by about 0.0075 inches high, although other dimensions can be used in other embodiments.

In an exemplary embodiment, the central lumen 51 extends through the length of the tubular body 12. As illustrated in FIG. 1, the central lumen 51 has a distal exit port 29 and a proximal access port 31. The proximal access port 31 forms part of the backend hub 33, which is attached to the tubular body proximal region 14. In such embodiments, the backend hub also includes a fluid fitting 46, which is hydraulically connected to the central lumen 51. In such embodiments, the backend hub 33 also includes a therapeutic compound inlet port 32, which is hydraulically coupled to the fluid delivery lumens 30, and which can also be hydraulically coupled to a source of therapeutic compound via a hub such as a Luer fitting.

Figure 3:
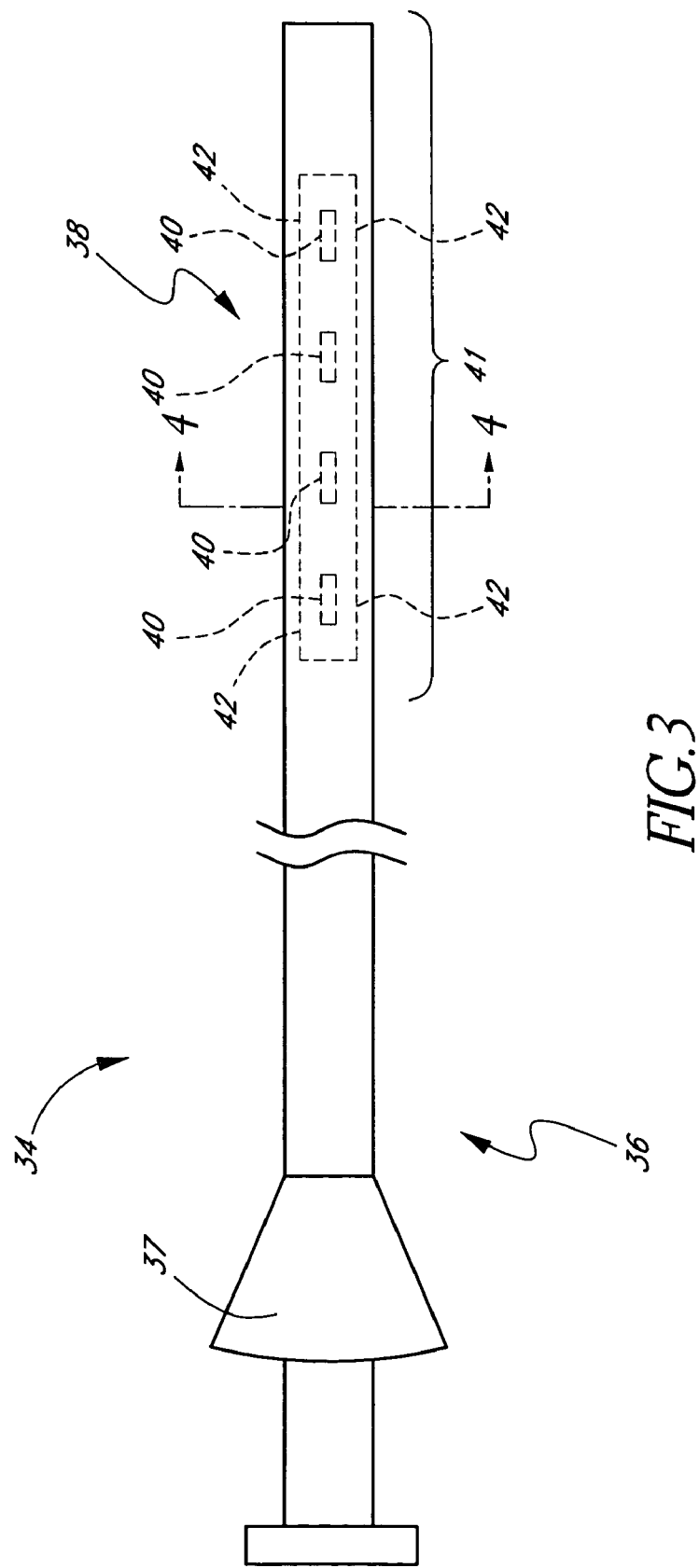
FIG. 3 is a schematic illustration of an elongate inner core configured to be positioned within the central lumen of the catheter illustrated in FIG. 2.

The central lumen 51 is configured to receive an elongate inner core 34, an exemplary embodiment of which is illustrated in FIG. 3. In such embodiments, the elongate inner core 34 includes a proximal region 36 and a distal region 38. A proximal hub 37 is fitted on one end of the inner core proximal region 36. One or more heating members 40 are positioned within an inner core energy delivery section 41 that is located within the distal region 38. The heating members 40 form a heating assembly 42, which will be described in greater detail below.

Figure 4:
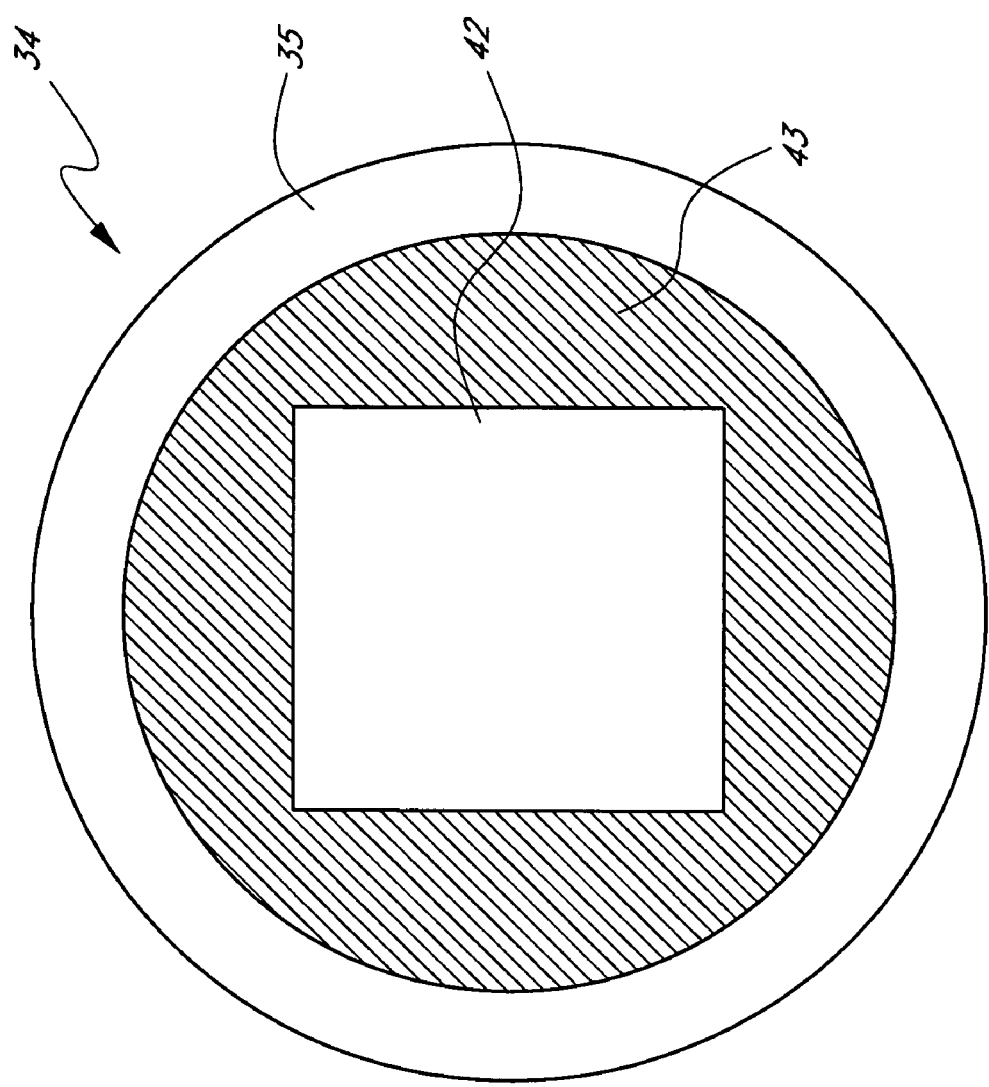
FIG. 4 is a cross-sectional view of the elongate inner core of FIG. 3 taken along line 4—4.

As shown in the cross-section illustrated in FIG. 4, which is taken along lines 4—4 in FIG. 3, in an exemplary embodiment, the inner core 34 has a cylindrical shape, with an outer diameter that permits the inner core 34 to be inserted into the central lumen 51 of the tubular body 12 via the proximal access port 31. Suitable outer diameters of the inner core 34 include, but are not limited to, between about 0.010 inches and about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 includes a cylindrical outer body 35 that houses the heating assembly 42. The heating assembly 42 includes wiring and heating members 40, described in greater detail in below, such that the heating assembly 42 is capable elevating the temperature of the treatment site as described below. For embodiments where the heating assembly is driven by an electrical current, the heating assembly 42 is electrically connected to the backend hub 33, where the inner core 34 can be connected to a control system 100 via cable 45 (illustrated in FIG. 1). In an exemplary embodiment, an electrically insulating potting material 43 fills the inner core 34, surrounding the heating assembly 42, thus reducing or preventing movement of the heating assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
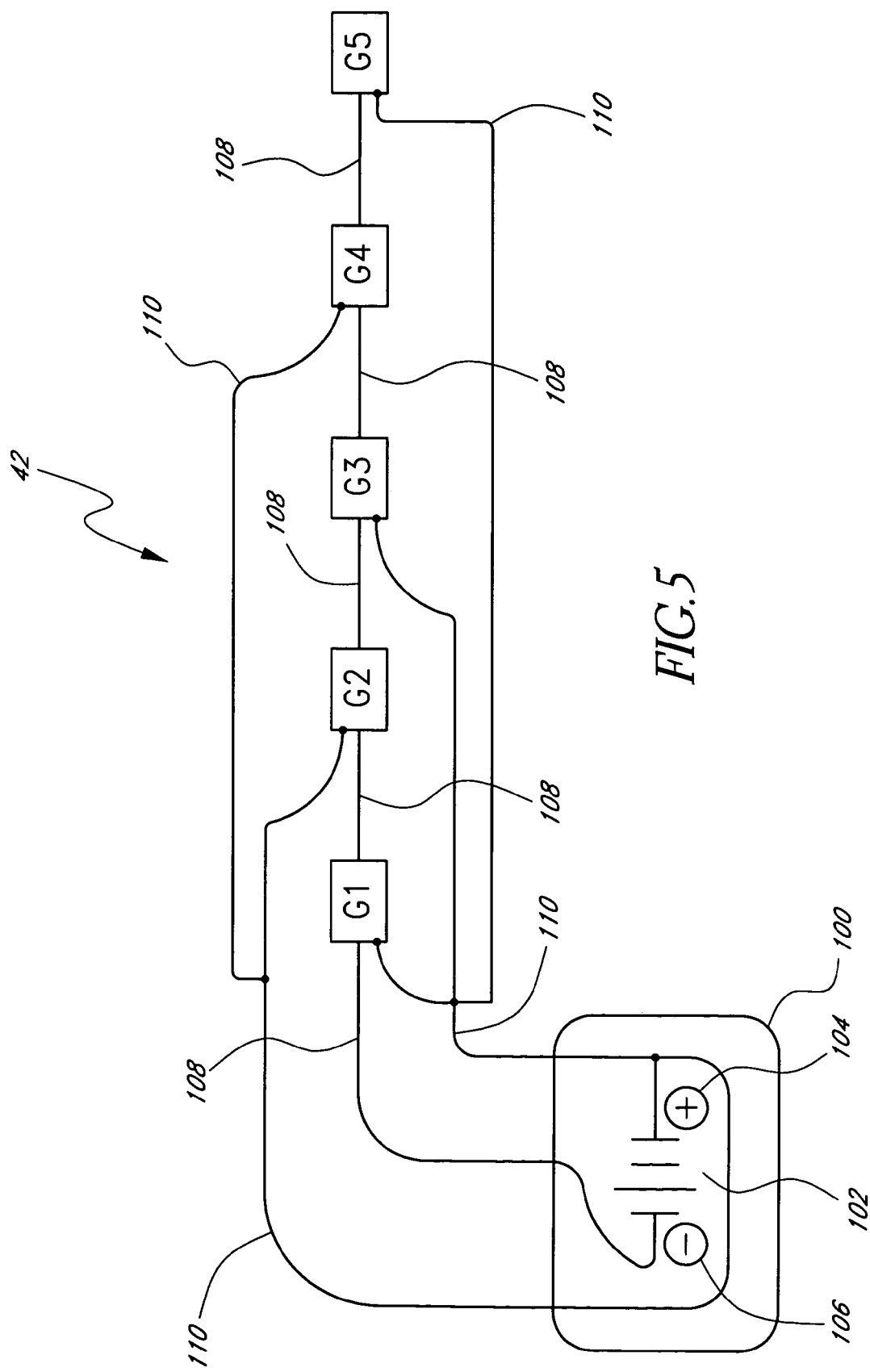
FIG. 5 is a schematic wiring diagram illustrating an exemplary technique for electrically connecting five groups of heating members to form an ultrasound assembly.

In an exemplary embodiment, the heating assembly 42 includes a plurality of heating members 40 that are divided into one or more groups. For example, FIG. 5 is schematic wiring diagram illustrating one technique for connecting five groups of heating members 40, in which the heat source members comprise an ultrasound element or a resistive heater. As illustrated in FIG. 5, the heating assembly 42 comprises five groups G1, G2, G3, G4, G5 of heating members 40 that are electrically connected to each other. The five groups are also electrically connected to the control system 100.

Still referring to FIG. 5, in an exemplary embodiment, the control circuitry 100 includes a voltage source 102 having a positive terminal 104 and a negative terminal 106. The negative terminal 106 is connected to common wire 108, which connects the five groups G1–G5 of heating members 40 in series. The positive terminal 104 is connected to a plurality of lead wires 110, which each connect to one of the five groups G1–G5 of heating members 40.

Figure 6:
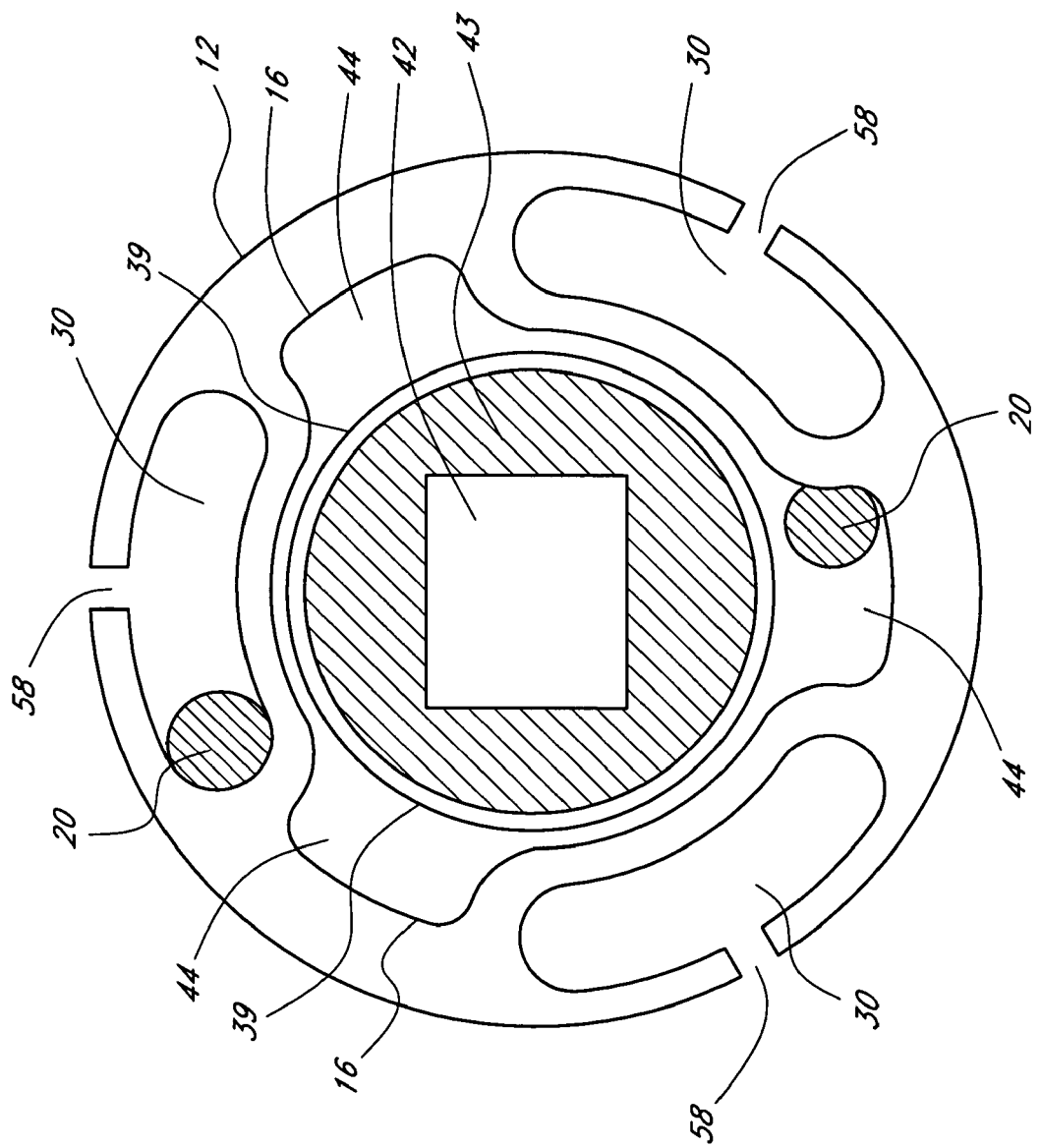
FIG. 6 illustrates the energy delivery section of the inner core of FIG. 4 positioned within the energy delivery section of the tubular body of FIG. 2.

FIG. 6 illustrates the inner core 34 positioned within the tubular body 12. As described above, the inner core 34 can be slid within the central lumen 51 of the tubular body 12, thereby allowing the inner core energy delivery section 41 to be positioned within the tubular body energy delivery section 18. In one embodiment, the tubular body 12 is advanced to the treatment site over a guidewire. The guidewire may then be removed and the inner core 34 can be an be slid within the central lumen.

FIG. 6 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. A plurality of fluid delivery ports 58 can be positioned axially along the tubular body 12. Thus, a source of therapeutic compound coupled to the inlet port 32 provides a hydraulic pressure which drives the therapeutic compound through the fluid delivery lumens 30 and out the fluid delivery ports 58.

By spacing the fluid delivery lumens 30 around the circumference of the tubular body 12 substantially evenly, as illustrated in FIG. 6, a substantially uniform flow of therapeutic compound around the circumference of the tubular body 12 can be achieved. Additionally, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters than fluid delivery ports closer to the distal region of the energy delivery section 18, thereby allowing uniform delivery of therapeutic compound in the energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to about 0.0020 inches in the distal region of the energy delivery section 18. The increase in size between adjacent fluid delivery ports 58 depends on a variety of factors, including the material comprising the tubular body 12, and on the size of the fluid delivery lumen 30. The fluid delivery ports 58 can be created in the tubular body 12 by punching, drilling, burning or ablating (such as with a laser), or by other suitable methods. Therapeutic compound flow along the length of the tubular body 12 can also be increased by increasing the density of the fluid delivery ports 58 toward the distal region of the energy delivery section.

In certain applications, a spatially nonuniform flow of therapeutic compound from the fluid delivery ports 58 to the treatment site is to be provided. In such applications, the size, location and geometry of the fluid delivery ports 58 can be selected to provide such nonuniform fluid flow.

Referring still to FIG. 6, placement of the inner core 34 within the tubular body 12 further defines fluid lumens 44. Fluid lumens 44 are formed between an outer surface 39 of the inner core 34 and an inner surface 16 of the tubular body 12. As explained in more detail below, a cooling or heating fluid can be introduced through the proximal access port 31 such that fluid flows through cooling fluid lumens 44 and out of the catheter 10 through distal exit port 29 (see FIG. 1). In an exemplary embodiment, the fluid lumens 44 are substantially evenly spaced around the circumference of the tubular body 12 (that is, at approximately 120° increments for a three-lumen configuration), thereby providing substantially uniform fluid flow over the inner core 34. Such a configuration can advantageously be used to remove or add thermal energy from the treatment site. As will be explained below, the flow rate of the fluid and the power to the heat source assembly 42 can be adjusted to maintain the temperature of the inner core energy delivery section 41, or of the treatment site generally, within a desired range.

In an exemplary embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, in an exemplary embodiment, the inner core outer body 35 comprises a material having the ability to transmit torque. Suitable materials for the inner core outer body 35 include, but are not limited to, polyimides, polyesters, polyurethanes, thermoplastic elastomers and braided polyimides.

In an exemplary embodiment, the fluid delivery lumens 30 and the fluid lumens 44 are open at the distal end of the tubular body 12, thereby allowing the therapeutic compound and the fluid to pass into the patient's vasculature at the distal exit port 29. In a modified embodiment, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can be prevented from passing through the distal exit port 29 by providing the inner core 34 with a length that is less than the length of the tubular body 12. In other embodiments, a protrusion is formed within the tubular body 12 in the distal region 15, thereby preventing the inner core 34 from passing through the distal exit port 29.

In other embodiments, the catheter 10 includes an occlusion device positioned at the distal exit port 29. In such embodiments, the occlusion device has a reduced inner diameter that can accommodate a guidewire, but that is less than the inner diameter of the central lumen 51. Thus, the inner core 34 is prevented from extending past the occlusion device and out the distal exit port 29. For example, suitable inner diameters for the occlusion device include, but are not limited to, between about 0.005 inches and about 0.050 inches. In other embodiments, the occlusion device has a closed end, thus preventing cooling fluid from leaving the catheter 10, and instead recirculating to the tubular body proximal region 14. These and other cooling fluid flow configurations permit the power provided to the ultrasound assembly 42 to be increased in proportion to the cooling fluid flow rate. Additionally, certain fluid flow configurations can reduce exposure of the patient's body to fluids.

In an exemplary embodiment, such as illustrated in FIG. 6, the tubular body 12 includes one or more temperature sensors 20 that are positioned within the energy delivery section 18. In such embodiments, the tubular body proximal region 14 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44. To maintain the axial position of the sensor 20 within the catheter 10 they may be attached to one or more elongated rigid members (not shown) that extend through the lumens 30.

Figure 7:
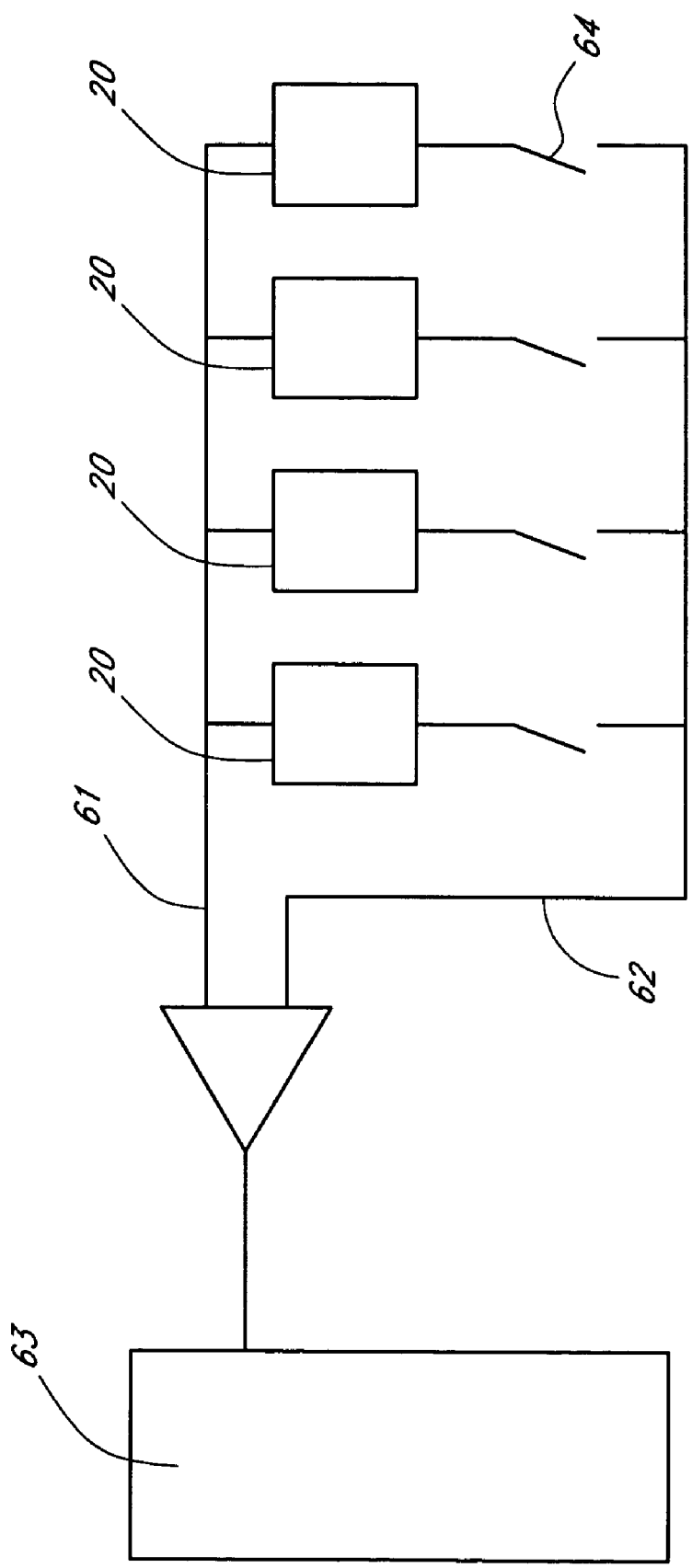
FIG. 7 illustrates a wiring diagram for connecting a plurality of temperature sensors with a common wire.

FIG. 7 illustrates an exemplary embodiment for electrically connecting the temperature sensors 20. In such embodiments, each temperature sensor 20 is coupled to a common wire 61 and is associated with an individual return wire 62. Accordingly, n+1 wires are passed through the tubular body 12 to independently sense the temperature at n temperature sensors 20. The temperature at a selected temperature sensor 20 can be determined by closing a switch 64 to complete a circuit between the return wire 62 associated with the selected thermocouple and the common wire 61. In embodiments wherein the temperature sensors 20 are thermocouples, the temperature can be calculated from the voltage in the circuit using, for example, a sensing circuit 63, which can be located within the external control circuitry 100.

In other embodiments, the temperature sensors 20 can be independently wired. In such embodiments, 2n wires are passed through the tubular body 12 to independently sense the temperature at n temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Overview of a Small Vessel Ultrasonic Catheter.

Figure 8A:
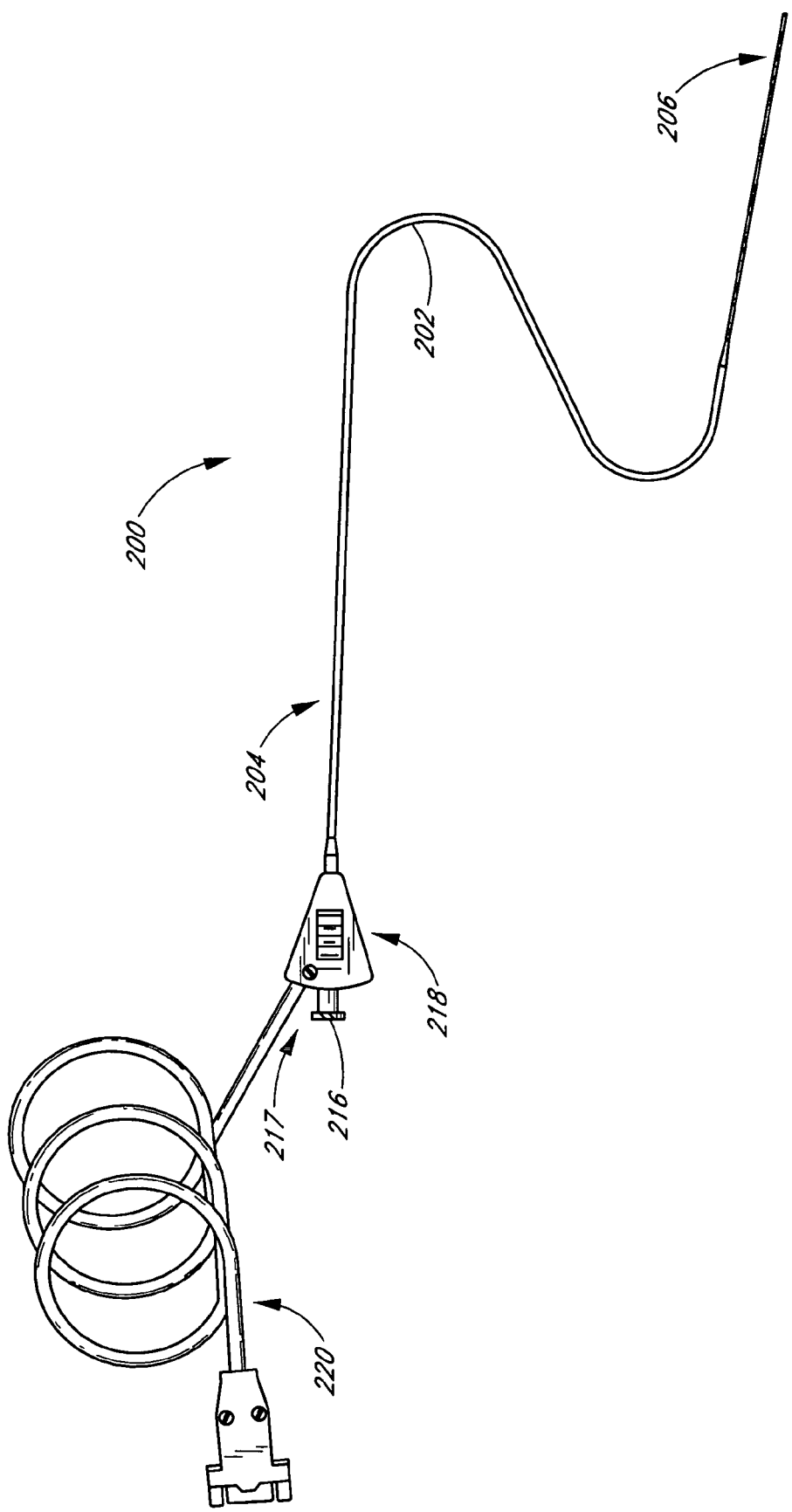
FIG. 8A is a schematic illustration of an ultrasonic catheter configured for insertion into small vessels of the human body.

FIGS. 8A–8C illustrate an exemplary catheter 200 that is specifically configured to effectively navigate the small vessels of a patient's vasculature, such as the main and subsequent branches of the middle cerebral artery.

Similar to the large vessel ultrasonic catheter described herein, an exemplary ultrasonic catheter configured for use in small vessels comprises a multi-component tubular body 202 having a proximal region 204 and a distal region 206. In such embodiments, the catheter tubular body 202 includes an outer sheath 208 that is positioned upon an inner core 210. In one embodiment, the outer sheath 208 comprises extruded Pebax®, PTFE, polyetheretherketone ("PEEK"), PE, polyamides, braided polyamides and/or other similar materials. The outer sheath distal region 206 is adapted for advancement through vessels having a small diameter, such as those in the vasculature of the brain. In an exemplary embodiment, the outer sheath distal region 206 has an outer diameter between about 2 French and about 5 French. In another embodiment, outer sheath distal region 206 has an outer diameter of about 2.8 French. In one exemplary embodiment, the outer sheath 208 has an axial length of approximately 150 centimeters.

In a modified embodiment, the outer sheath 208 comprises a braided tubing formed of, for example, high or low density polyethylenes, urethanes, nylons, and the like. This configuration enhances the flexibility of the tubular body 202. For enhanced maneuverability, especially the ability to be pushed and rotated, the outer sheath 208 can be formed with a variable stiffness from the proximal to the distal end. To achieve this, a stiffening member may be included along the proximal end of the tubular body 202.

The inner core 210 defines, at least in part, a delivery lumen 212, which, in an exemplary embodiment, extends longitudinally along the catheter. The delivery lumen 212 has a distal exit port 214, and is hydraulically connected to a proximal access port (not shown). Similar to the large vessel ultrasonic catheter described herein, the proximal access port can be connected to a source of therapeutic compound or cooling/heating fluid that is to be delivered through the delivery lumen 212.

In an exemplary embodiment, the delivery lumen 212 is configured to receive a guide wire (not shown). In such embodiments, the guidewire has a diameter of between approximately 0.008 and approximately 0.012 inches. In another embodiment, the guidewire has a diameter of about 0.010 inches. In an exemplary embodiment, the inner core 210 comprises polyamide or a similar material which can optionally be braided to increase the flexibility of the tubular body 202 and reduce kinking and/or binding with the guidewire.

With reference to FIGS. 8B and 8C, the tubular body distal region 206 includes a heating member 224. As mentioned above, the heating element 224 may comprise any of a variety of components, such as, for example, thermoelectric devices, ultrasound transducers, etc. In the illustrated embodiment, the heating element 224 is configured as a hollow cylinder or otherwise generally disposed between the inner core 210 and the outer sheath 208. As such, the inner core 210 extends generally through the lumen of the heating member 224. The heating member 224 may be secured to the inner core 210 in a suitable manner, such as using an adhesive. A potting material can also be used to further secure the heating member 224 to the inner core 210.

In the illustrated embodiment, thermal energy is generated from electrical power supplied to the heating member 224 through a wires 226, 228 that extend through the catheter body 202. The wires 226, 228 cab be secured to the inner core 210, lay along the inner core 210 and/or extend freely in the region 238 between the inner core 210 and the outer sheath 208. In embodiments wherein the heating member 224 comprises a transducer formed of a piezoelectric ceramic oscillator or a similar material, the first wire 226 may be connected to the hollow center of the ultrasound radiating member 224, while the second wire 228 is connected to the outer periphery of the ultrasound radiating member 224.

Still referring to the exemplary embodiment illustrated in FIGS. 8A–8D, the catheter further includes a sleeve 230 that is generally positioned about the heating member 224. The sleeve 230 is comprises a material that readily transmits thermal energy. Suitable materials for the sleeve 230 include, but are not limited to, polyolefins, polyimides, polyester and other materials having a relatively low absorbance of ultrasonic energy. The proximal end of the sleeve 230 can be attached to the outer sheath 208 with an adhesive 232. To improve the bonding of the adhesive 232 to the outer sheath 208, a shoulder 227 or notch can be formed in the outer sheath 208 for attachment of the adhesive 232 thereto. In an exemplary embodiment, the outer sheath 208 and the sleeve 230 have substantially the same outer diameter.

In a similar manner, the distal end of the sleeve 230 can be attached to a tip 234. As illustrated, the tip 234 is also attached to the distal end of the inner core 210. In an exemplary embodiment, the tip 234 is between about 0.5 mm and about 4.0 mm long. In another embodiment, the tip is about 2.0 mm long. In the illustrated exemplary embodiment, the tip 234 is rounded in shape to reduce trauma or damage to tissue along the inner wall of a blood vessel or other body structure during advancement of the catheter to a treatment site.

Referring now to the exemplary embodiment illustrated in FIG. 8CB, the catheter includes at least one temperature sensor 236 in the tubular body distal region 206. The temperature sensor 236 can be positioned on or near the heating member 224. Suitable temperature sensors include but are not limited to, diodes, thermistors, thermocouples, RTDs and fiber optic temperature sensors that used thermalchromic liquid crystals. In an exemplary embodiment, the temperature sensor 236 is operatively connected to a control system via a control wire that extends through the tubular body 202. As described below, the control box includes a feedback control system having the ability to monitor and control the power, voltage, current and phase supplied to the heating member 224. Thus, the temperature along the relevant region of the catheter can be monitored and controlled for optimal performance.

As mentioned above, the distal exit port 214 and heating member 224 are generally positioned at the distal end 206 of the catheter to form a treatment zone 250, which is configured to elevate the temperature of the treatment site and to deliver a therapeutic compound to the treatment site.

Controlled Thermal Effects.

The catheters 10, 200 described above can be used to elevate the temperature of the treatment site. They may also be used to deliver a therapeutic compound to the treatment site. The elevated temperature may enhance the efficacy of certain therapeutic compounds by altering the structure of the therapeutic compound and/or effecting (e.g., accelerating) the chemical reactions at the treatment site. As explained below, the elevated temperature may be used alone or in combination with ultrasound energy to enhance the therapeutic effect of a therapeutic compound. In one embodiment, the therapeutic compound is a compound that is used for the treatment of vascular occlusions, such as, for example, heparin, urokinase, streptokinase, tPA, rtPA and BB-10153 (manufactured by British Biotech, Oxford, UK) and/or other thrombolytic compounds or anti-thrombosis compounds. In such an embodiment, the heating element(s) may be used to raise the temperature of the treatment site, which includes the vascular occlusion that is targeted by the therapeutic compound. In this manner, the elevated temperature enhances the treatment and removal of the vascular occlusion. While thermal effects can be beneficial, it should be appreciated excessively high temperatures can cause tissue damage and death. Accordingly, in the preferred embodiments, the elevated temperature is kept within a safe limit, which, in one embodiment, is less than or equal to about 43° C.

Figure 9:
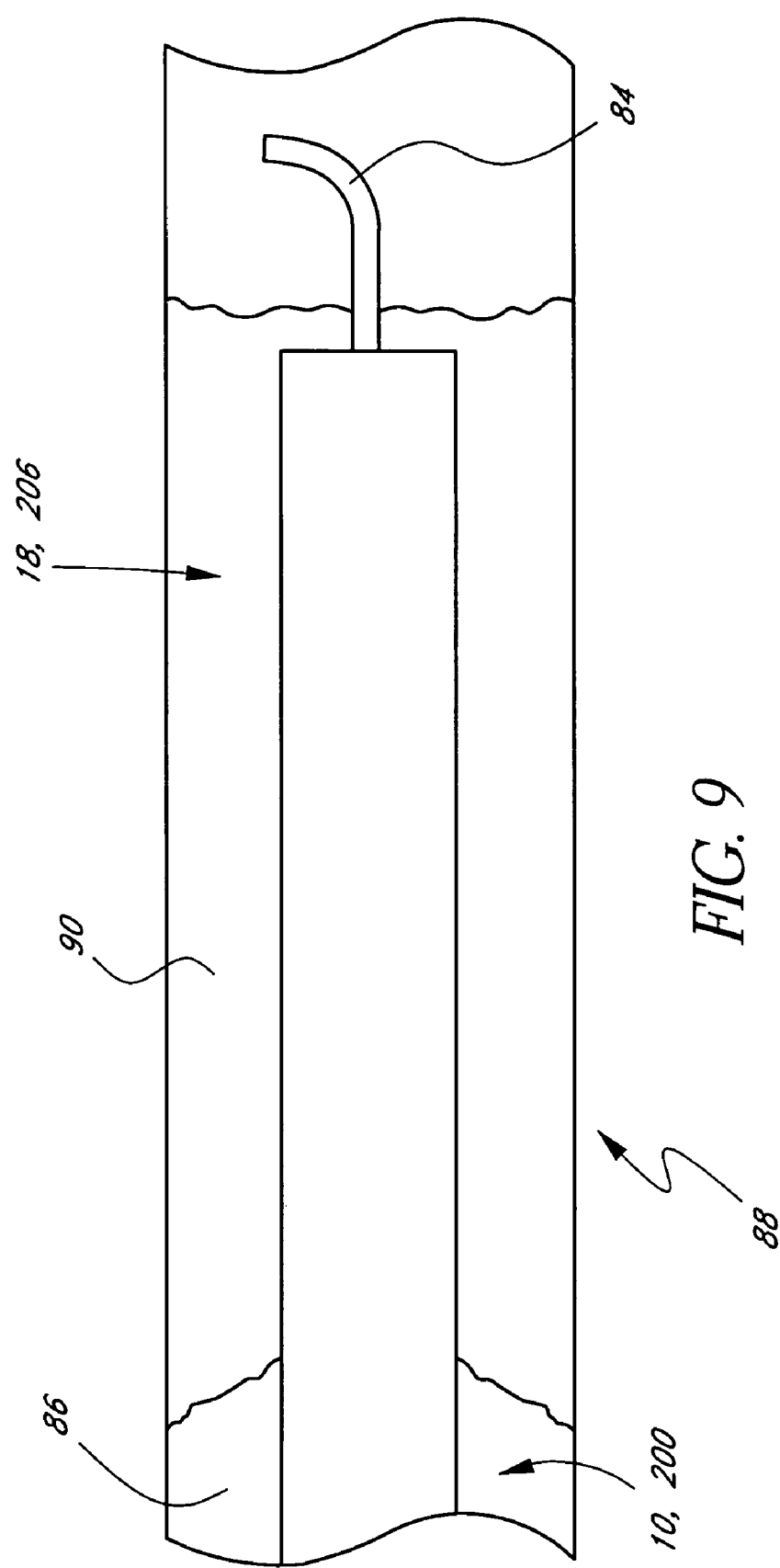
FIG. 9 is a side view of the distal end of an ultrasonic catheter positioned at a treatment site.
Figure 10:
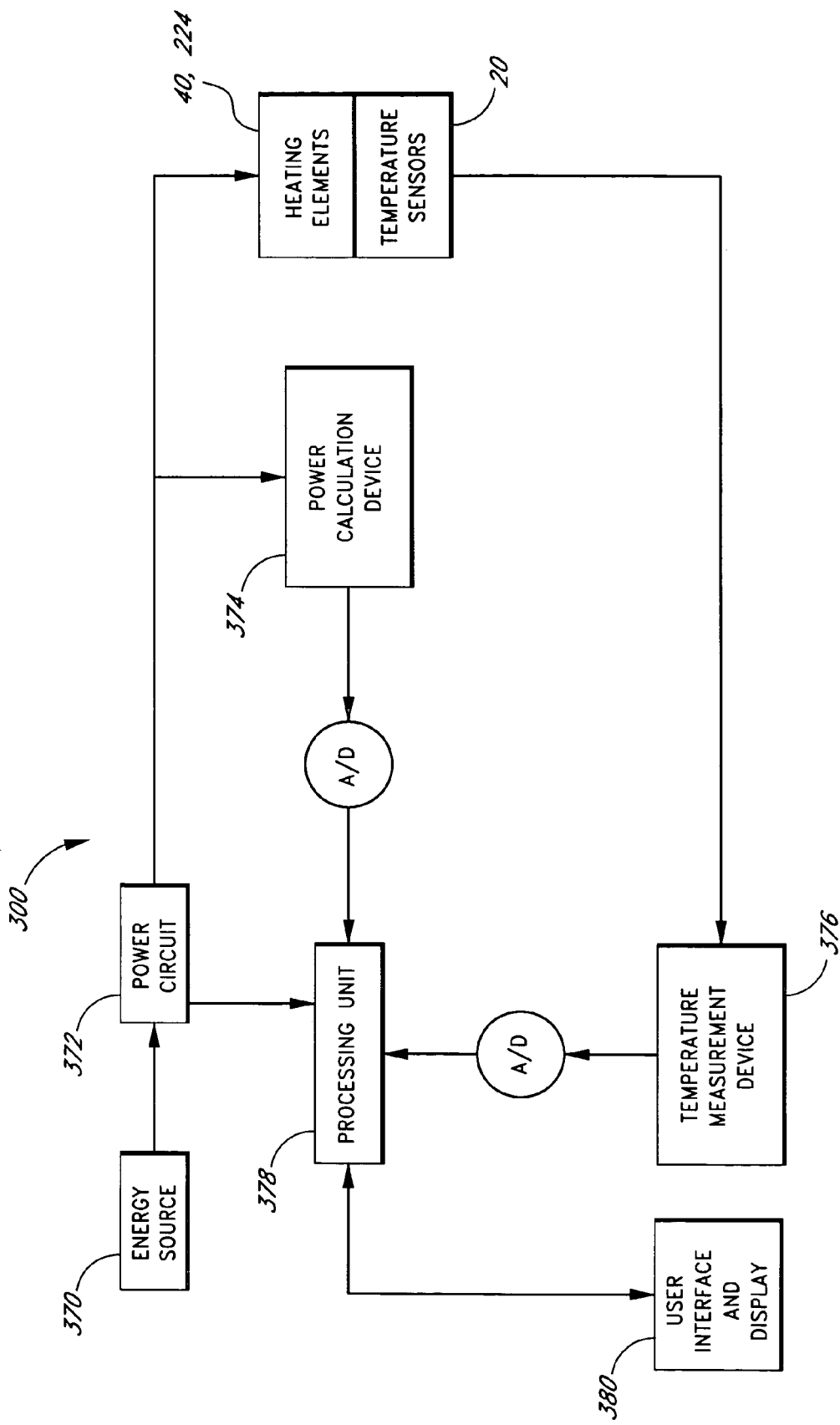
FIG. 10 is a block diagram of a feedback control system for use with an ultrasonic catheter.

As shown in FIG. 9, the catheter 10, 100 of FIGS. 1–7 or 8A–8C may be advanced over a guidewire 84 to a treatment site 88 that includes a obstruction or clot 90. The guidewire 84 is optionally directed through the clot 90. The catheter 10, 100 is then advanced until the treatment zone is positioned at that treatment site. In this position, the treatment zone may be positioned partially or wholly within the clot 90. In other embodiments, the treatment zone or portions thereof including either the heating elements and/or the drug delivery port(s) (not shown in FIG. 9) may be positioned either upstream or downstream of the clot 90. With respect to the embodiments of FIGS. 1–7, it should be understood that the guidewire 84 is typically removed before the inner core 34 is advanced to the treatment site 88.

With the catheter 10, 100 in place, the heating element(s) may be used to elevate the temperature of the treatment site. The therapeutic compound can be delivered before, after, during or intermittently with the activation of the heating element(s). In one embodiment, the treatment site is maintained at an elevated (as compared to ambient conditions) temperature. In one embodiment, the elevated temperature is at least about 38° C. In another embodiment, the elevated temperature is at least about 40° C. In another embodiment, the treatment site is maintained within elevated temperature range, which in one embodiment is about from about 38 to about 43° C. In one embodiment, the treatment site is maintained at the elevated temperature for at least 5 minutes, in another embodiment at least 15 minutes, and in still another embodiment at least 30 minutes. In yet another embodiment, the treatment site is maintained at the elevated temperature until the clot 90 is substantially dissolved and/or blood flow through the vessel is substantially reestablished to normal conditions. As mentioned above, the therapeutic compound may be delivered before, during and/or intermittingly during the treatment. Once the clot 90 has been sufficiently dissolved, the catheter can be withdrawn from the treatment site 88.

As explained above, the elevated temperature enhances the therapeutic effect of the therapeutic compound. In one embodiment, this results faster dissolution of clot. In another embodiment, the clot can be dissolved with less therapeutic compound as compared to treatment without the elevated temperature. Both embodiments are advantageous in that the therapeutic compound may have adverse side affects.

As mentioned above, the heat element may be any of a variety of components configured to deliver heat to a treatment site within a vascular system. In one embodiment, the heat source comprises an ultrasound transducer. With respect to ultrasonic transducers, thermal energy is generated in two ways. First, because the ultrasonic transducer coverts electrical energy to ultrasound energy imperfectly, some portion of the electrical energy is converted to heat. In addition, it is postulated that the ultrasound filed generated by the transducer is absorbed by the biological material surrounding the catheter producing a localized elevation of temperature. In such an embodiment, ultrasound energy can be applied to the treatment site along with the thermal energy. In another embodiment, the heat source comprises an modified ultrasound element that is configured to covert a larger percentage of electrical converted to heat as compared to the ultrasound elements optimized for the production of ultrasound energy.

In still another embodiment, the heat source comprises thermoelectric device, such as, a resistant heater through which heat is generated by passing an electrical current therethrough. In another embodiment, a heated solution (e.g., the therapeutic compound it self or a fluid passes through the lumen 44 of FIG. 6) can be delivered through the catheter to the treatment zone or the treatment site. In yet another embodiment, a RF element can be used to apply RF energy to raise the temperature of the treatment site.

In any of these embodiments, the catheters 10, 200 optionally include a control system capable of monitoring the temperature at the treatment site, and adjusting the operating parameters of the catheter accordingly. FIG. 100 is one example of such a control system 300, which his configured to control an embodiment in which the heating element 40, 224 comprises a thermoelectric device (e.g., a resistive heater or an ultrasound element). In light of the disclosure herein, those of skill in the art will recognize how to adapted the control system 68 to other types of heating elements.

The feedback control system 300 includes an energy source 370, power circuits 372 and a power calculation device 374 that is coupled to the heating element 40, 224. A temperature measurement device 376 is coupled to the temperature sensor 20, 236 in the catheter 10, 200. A processing unit 378 is coupled to the power calculation device 374, the power circuits 372 and a user interface and display 380.

In an exemplary method of operation, the temperature at the temperature sensor 20, 236 is determined by the temperature measurement device 376. The processing unit 378 receives each determined temperature from the temperature measurement device 376. The determined temperature can then be displayed to the user at the user interface and display 380.

In an exemplary embodiment, the processing unit 378 includes logic for generating a temperature control signal. The temperature control signal is proportional to the difference between the measured temperature and a desired temperature. The desired temperature can be determined by the user (as set at the user interface and display 380) or can be preset within the processing unit 378.

In such embodiments, the temperature control signal is received by the power circuits 372. The power circuits 372 are configured to adjust the power level, voltage, phase, duty cycle and/or current of the electrical energy supplied to the heating elements 40, 224 from the energy source 370. For example, when the temperature control signal is above a particular level, the power supplied to the heat element is reduced in response to that temperature control signal. Similarly, when the temperature control signal is below a particular level, the power supplied to the heating source is increased in response to that temperature control signal. After each power adjustment, the processing unit 378 monitors the temperature sensors 20, 236 and produces another temperature control signal which is received by the power circuits 372.

The processing unit 378 can comprise a digital or analog controller, such as a computer with software. In embodiments wherein the processing unit 78 is a computer, the computer can include a central processing unit ("CPU") coupled through a system bus. In such embodiments, the user interface and display 380 can include a mouse, a keyboard, a disk drive, a display monitor, a nonvolatile memory system, and/or other computer components. In an exemplary embodiment, program memory and/or data memory is also coupled to the bus.

Figure 11:
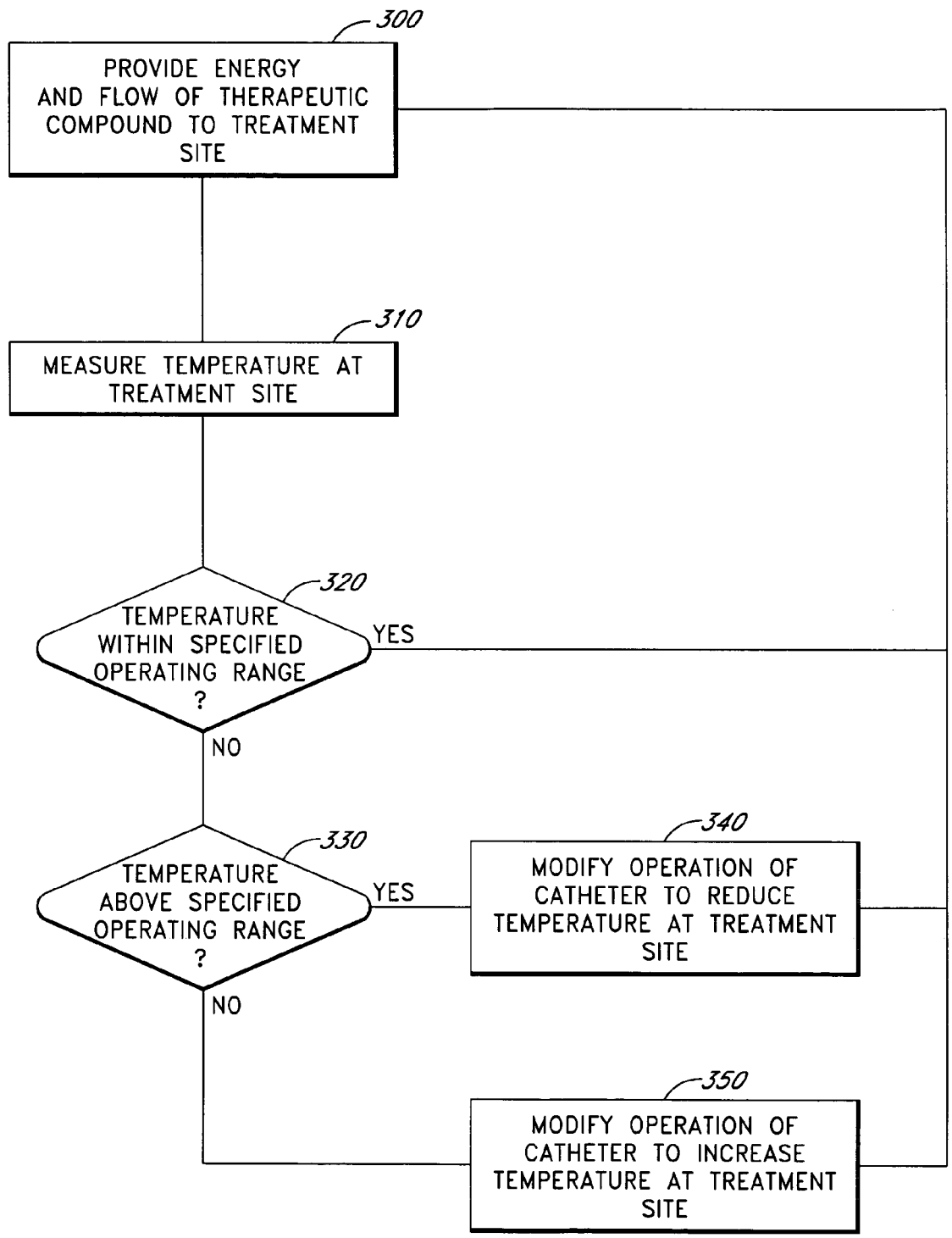
FIG. 11 is a flowchart illustrating an exemplary technique for manipulating the temperature of a therapeutic compound at a treatment site.

An exemplary control routine that can be utilized by the control system to maintain the temperature of the treatment site is illustrated in FIG. 11. In this technique, a therapeutic compound and thermal energy are delivered from a catheter located at the treatment site in an operational block 300.

Once delivery of the therapeutic compound and the ultrasonic energy is established, the temperature of the treatment site is monitored in an operational block 310. Using the control system described herein, the measured temperature is compared to a specified operating range at decision points 320, 330. If the measured temperature is within the specified operating range, the treatment continues unchanged. However, if the measured temperature is above the specified range, the operation of the catheter is modified to reduce the temperature of the treatment site in an operational block 340. Likewise, if the measured temperature is below the specified range, the operation of the catheter is modified to increase the temperature of the treatment site in an operational block 340.

It should be appreciated that the process of maintaining the elevated temperature of the treatment site will vary depending upon the nature of the heat heating element. For example, in one embodiment, the temperature can be controlled by increasing or decreasing the flow rate of a heating fluid or a cooling fluid. In another embodiment, the flow and/or temperature of the therapeutic compound may be used to maintain the treatment site at the elevated temperature. increasing the temperature of the therapeutic compound provided to the therapeutic compound inlet port at the catheter proximal end. In still other embodiments, the temperature is decreased by simply reducing the power supplied to the heating elements.

In one modified embodiment, the thermal energy and the therapeutic compound can be delivered to the treatment site with different components. For example, in one embodiment, the therapeutic compound is delivered through a drug delivery catheter advanced to the treatment site. The heat source may be advanced to the treatment site via a second component, such as, a second separate catheter or an element (e.g., a guidewire or inner core) that is advanced through or along side the drug delivery catheter. The two components may be positioned adjacent to each other during treatment or one of the components may be removed when not in use.

In still another embodiment, the elevated temperature at treatment site can be generated from an energy source that is external to the body. For example, ultrasound energy can be provided to the treatment site by applying an ultrasound transducer against the external surface tissue surrounding the target vessel. For example, for the neurovascular system, the external transducer may be applied against the head. The are two general external application strategies: A) Low frequency (e.g., 40 KHz to 200 KHz), unfocused ultrasound which has the advantage of easier penetration but must necessarily irradiate a larger area (see e.g., U.S. Pat. Nos. 6,113,570, 6,575,922, 5,695460 and 5,399,158, which are incorporated by reference in their entirety); or B) higher frequency (e.g. >2 MHZ), focused ultrasound which can be directed towards the treatment site. With respect to the higher frequency technique, because of its less efficient transmissivity, it is common to apply the ultrasound through specific anatomic "windows" (e.g., the temple; above and in front of the ears for neurovascular applications) (see e.g., U.S. Pat. No 6,733,450, which is incorporated by reference in its entirety).

In these embodiments, the therapeutic compound can be applied to the treatment site via a drug delivery catheter. The treatment site may be heated using the external ultrasound techniques described above. The ultrasound is absorbed the biological material producing a elevation of temperature at the treatment site. The drug delivery catheter may be provided with a temperature sensor to monitor the temperature at the treatment site.

As described above, the elevated temperature may be used in combination with therapeutic ultrasound therapy. See e.g., U.S. Patent Application Nos. 2004/0024347, filed Dec. 3, 2002, and 2004/0049148, filed Dec. 3, 2002, which are hereby incorporated by reference herein. In such embodiments, the heating elements may comprise ultrasound radiating members and/or ultrasound radiating members may be integrated into the catheter described above. In such embodiments, the suitable frequencies for the ultrasound radiating members 40 include, but are not limited to, from about 20 kHz to about 20 MHz. In one embodiment, the frequency is between about 500 kHz and about 20 MHz, and in another embodiment the frequency is between about 1 MHz and about 3 MHz. In yet another embodiment, the ultrasound radiating members 40 are operated with a frequency of about 2 MHz.

In another embodiment, the heating element in the catheter is configured to heat the therapeutic compound as it flows through the catheter towards the treatment site. In this manner, a therapeutic compound with an elevated temperature can be delivered to the treatment site. The elevated temperature of the compound will also elevate the temperature of the treatment site.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

We claim:

1. A method of treating a vascular obstruction at a treatment site within a patient's vascular system, the method comprising:
   advancing a catheter to the treatment site, the catheter including a treatment zone, the catheter comprising a fluid delivery lumen that is coupled to an exit port within the treatment zone of the catheter;
   passing a therapeutic compound through the fluid delivery lumen and the exit port, such that the therapeutic compound is delivered to the treatment site;
   heating the treatment site to an elevated temperature; and
   increasing a blood carrying capacity of the treatment site.

2. The method of claim 1, further comprising maintaining the elevated temperature of the treatment site for at least five minutes.

3. The method of claim 1, further comprising maintaining the elevated temperature of the treatment site for at least thirty minutes.

4. The method of claim 1, further comprising maintaining the elevated temperature of the treatment site until blood flow through the treatment site is substantially reestablished.

5. The method of claim 1, wherein heating the treatment site to an elevated temperature comprises applying ultrasound energy to the treatment site.

6. The method of claim 1, wherein heating the treatment site to an elevated temperature comprises activating a heating element positioned within a treatment zone of the catheter.

7. The method of claim 6, wherein activating a heating element positioned within a treatment zone of the catheter comprises providing electrical power to the heat source.

8. The method of claim 6, wherein activating a heating element positioned within a treatment zone of the catheter comprises providing a heated fluid to the heat source.

9. The method of claim 1, further comprising measuring a temperature at the treatment site.

10. The method of claim 1, wherein advancing a catheter to the treatment site comprises advancing the catheter through a portion of the patient's neurovascular system.

11. The method of claim 1, wherein advancing a catheter to the treatment site comprises advancing the catheter through a portion of the patient's leg.

12. The method of claim 1, wherein the elevated temperature is greater than about 38 degrees Celsius.

13. The method of claim 1, wherein the elevated temperature is greater than about 40 degrees Celsius.

14. The method of claim 1, wherein the elevated temperature is less than about 43 degrees Celsius.

15. The method of claim 1, wherein the elevated temperature is within the range of about 38 degrees Celsius to about 43 degrees Celsius.

16. A catheter comprising;
- a tubular body having a fluid delivery lumen that is hydraulically coupled to an exit port within a treatment zone;
- a heating element positioned within the treatment zone;
- a temperature sensor in the treatment zone; and
- a control system configured to maintain the treatment zone at an elevated temperature for a specified amount of time, wherein the specified amount of time is sufficient to increase the blood carrying capacity of the treatment zone.

17. A catheter as in claim 16, wherein the heating element comprises an ultrasound element.

18. A catheter as in claim 16, wherein the catheter is configured such that the treatment zone may be advanced into the main and subsequent branches of the middle cerebral artery.

19. A catheter as in claim 16, wherein the heating element is configured to heat a therapeutic compound flowing through the fluid delivery lumen.

20. The catheter of claim 19, wherein the heating element is configured to heat the therapeutic compound before it passes through the exit port.

* * * * *